(12) United States Patent
Blier

(10) Patent No.: US 8,728,120 B2
(45) Date of Patent: *May 20, 2014

(54) BIOMECHANICAL FASTENER

(71) Applicant: Covidien LP, Mansfield, MA (US)

(72) Inventor: Kenneth M. Blier, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/896,491

(22) Filed: May 17, 2013

(65) Prior Publication Data

US 2013/0248579 A1 Sep. 26, 2013

Related U.S. Application Data

(60) Continuation of application No. 13/666,995, filed on Nov. 2, 2012, now Pat. No. 8,465,520, which is a division of application No. 13/367,394, filed on Feb. 7, 2012, now Pat. No. 8,323,314, which is a continuation of application No. 13/284,134, filed on Oct. 28, 2011, now Pat. No. 8,343,184, which is a continuation of application No. 12/137,702, filed on Jun. 12, 2008, now abandoned.

(60) Provisional application No. 60/934,254, filed on Jun. 12, 2007.

(51) Int. Cl.
*A61B 17/08* (2006.01)

(52) U.S. Cl.
USPC ............. 606/219; 606/220; 606/75; 227/902; 411/457; 411/475; 411/920; 411/923

(58) Field of Classification Search
USPC ............. 606/219, 220, 75; 227/902; 411/457, 411/475, 920, 923
See application file for complete search history.

(56) References Cited

U.S. PATENT DOCUMENTS

| | | | |
|---|---|---|---|
| T958,003 I4 | 5/1977 | Russel et al. | |
| 5,497,934 A | 3/1996 | Brady et al. | |
| 5,503,320 A | 4/1996 | Webster et al. | |
| 5,535,937 A | 7/1996 | Boiarski et al. | |
| 6,645,205 B2 | 11/2003 | Ginn | |
| 6,671,185 B2 | 12/2003 | Duval | |
| 7,056,330 B2 * | 6/2006 | Gayton | 606/219 |
| 7,398,907 B2 | 7/2008 | Racenet et al. | |
| 7,717,312 B2 | 5/2010 | Beetel | |

(Continued)

FOREIGN PATENT DOCUMENTS

| | | |
|---|---|---|
| WO | WO02/20296 | 4/2002 |
| WO | WO03/049906 | 6/2003 |

OTHER PUBLICATIONS

European Search Report for corresponding EP 08251988 date of mailing is Oct. 17, 2008 (3 pages).

*Primary Examiner* — Melanie Tyson
*Assistant Examiner* — Todd J Scherbel

(57) ABSTRACT

According to an aspect of the present disclosure, a biomechanical fastener is provided and includes a backspan defining an upper surface, a lower surface and a pair of side surfaces; at least a pair of legs depending from the backspan; and at least one contact pad extending from the lower surface to the upper surface of the backspan. At least one of the pair of legs contacts at least one of the contact pads upon a formation thereof.

8 Claims, 8 Drawing Sheets

(56) References Cited

U.S. PATENT DOCUMENTS

| | | |
|---|---|---|
| 7,784,663 B2 | 8/2010 | Shelton, IV |
| 7,794,475 B2 * | 9/2010 | Hess et al. .................. 606/219 |
| 7,905,902 B2 | 3/2011 | Huitema et al. |
| 8,323,314 B2 * | 12/2012 | Blier ............................ 606/219 |
| 8,343,184 B2 * | 1/2013 | Blier ............................ 606/219 |
| 8,465,520 B2 * | 6/2013 | Blier ............................ 606/219 |
| 2004/0254608 A1 * | 12/2004 | Huitema et al. .............. 606/219 |
| 2006/0291981 A1 | 12/2006 | Viola et al. |
| 2008/0312687 A1 | 12/2008 | Blier |
| 2009/0318957 A1 | 12/2009 | Viola et al. |
| 2011/0309128 A1 | 12/2011 | Okoniewski |
| 2012/0228358 A1 | 9/2012 | Zemlok et al. |

\* cited by examiner

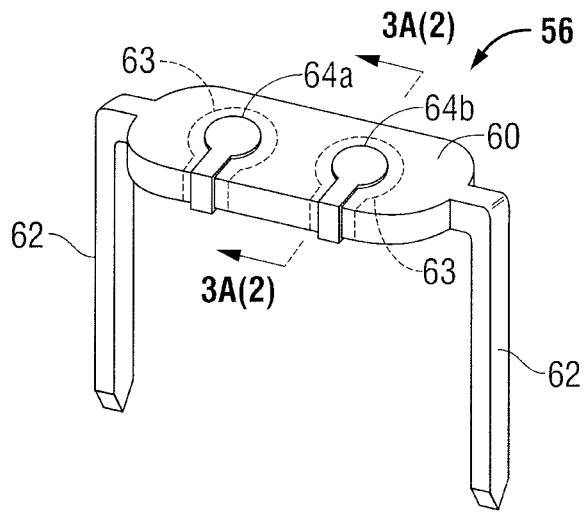
FIG. 3A
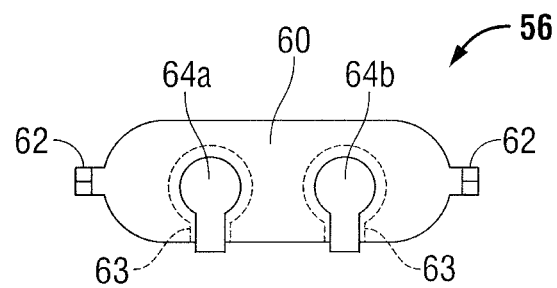
FIG. 3A(1)
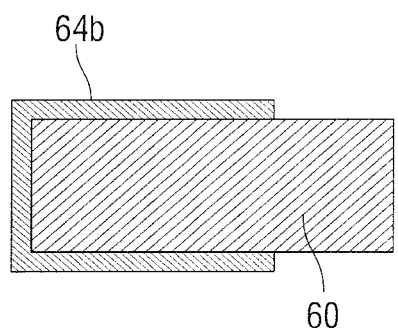
FIG. 3A(2)

BIOMECHANICAL FASTENER

CROSS-REFERENCE TO RELATED APPLICATION

The present application is a Continuation Application claiming the benefit of and priority to U.S. patent application Ser. No. 13/666,995 (now U.S. Pat. No. 8,465,520), filed on Nov. 2, 2012, which is a Divisional Application claiming the benefit of and priority to U.S. patent application Ser. No. 13/367,394, filed on Feb. 7, 2012 (now U.S. Pat. No. 8,323,314), which is a Continuation Application claiming the benefit of and priority to U.S. patent application Ser. No. 13/284,134, filed on Oct. 28, 2011 (now U.S. Pat. No. 8,343,184), which is a Continuation Application claiming the benefit of and priority to U.S. patent application Ser. No. 12/137,702, filed on Jun. 12, 2008, now abandoned, which claims the benefit of and priority to U.S. Provisional Application Ser. No. 60/934,254, filed on Jun. 12, 2007, now expired, the entire contents of each of which is incorporated herein by reference.

BACKGROUND

1. Technical Field

The present disclosure relates to surgical instruments and, more particularly, to biomechanical fasteners for use with mechanical surgical instruments, electro-mechanical surgical instruments and energy-based surgical instruments and systems.

2. Background of Related Art

Surgical instruments used in open and minimally invasive surgery are limited in their ability to sense and/or control conditions and/or parameters and factors critical to effective operation. For example, conventional surgical instruments cannot measurably detect the amount or degree of formation of the fastener(s) deployed therefrom in order to ascertain whether said fastener(s) are under-formed, over-formed or properly formed.

Proper formation of the fasteners is an important factor in tissue stapling. For example, if the fasteners are under-formed, the tissue secured thereby may not be compressed sufficiently in order to heal efficiently and properly. If the fasteners are over-formed, the tissue secured thereby may be over compressed and result in inefficient healing of the same.

Additionally, the determination of proper fastener formation is dependent upon the particular characteristics of the tissue being fastened. For example, if relatively thinner tissue or relatively highly vascular tissue is being fastened, then it may be desirable for the fasteners to be formed by a relatively greater degree. Likewise, if relatively thicker tissue or relatively less vascular tissue is being fastened, then it may be desirable for the fasteners to be formed by a relatively lesser degree.

Accordingly, a need exists for surgical instruments and/or systems that employ biomechanical fasteners and the like which enable proper fastener formation for particular surgical procedures and/or for particular tissues which are to be fastened.

SUMMARY

According to an aspect of the present disclosure, a surgical instrument for operating on tissue is provided. The surgical instrument includes an indicating circuit which is activated upon the proper formation of the surgical staples fired therefrom.

According to an aspect of the present disclosure, a biomechanical fastener is provided and includes a backspan defining an upper surface, a lower surface and a pair of side surfaces; at least a pair of legs depending from the backspan; and at least one contact pad extending from the lower surface to the upper surface of the backspan. At least one of the pair of legs contacts at least one of the contact pads upon a formation thereof.

In an embodiment, at least a portion of the backspan is non-conductive. The biomechanical fastener may further include a layer of non-conductive material interposed between the backspan and the contact pads.

The biomechanical fastener may further include a pair of contact pads supported on the backspan. Each contact pad may be operatively associated with a respective leg. In use, the legs may contact a respective contact pad upon formation thereof.

At least one leg and at least a respective contact pad may be fabricated from an electrically conductive material. In an embodiment, each leg and each contact pad may be fabricated from an electrically conductive material.

In an embodiment, at least one contact pad may extend from the lower surface to the upper surface of the backspan along at least one side surface of the backspan. In another embodiment, at least one contact pad mat extend through the backspan so as to be exposed at the upper surface and the lower surface of the backspan.

It is contemplated that each contact pad may be electrically isolated from one another.

According to another aspect of the present disclosure, a biomechanical fastener is provided and includes a backspan defining an upper surface and a lower surface, the backspan defining at least one aperture therein that extends completely from the upper surface through the lower surface; and at least a pair of legs depending from the backspan, wherein a free end of each leg extends through the at least one aperture formed in the backspan upon a formation of the fastener.

According to yet another aspect of the present disclosure, an electrosurgical system is provided and includes a fastening device including a cartridge assembly and an anvil assembly, wherein the anvil assembly is in juxtaposed relation relative to the cartridge assembly, wherein the cartridge assembly and the anvil assembly are movable between a spaced apart position and an approximated position, and wherein the cartridge assembly is configured to retain a plurality of fasteners therein and wherein the anvil assembly is configured to form the plurality of fasteners upon approximation of the cartridge assembly and the anvil assembly. The electrosurgical system further includes a plurality of biomechanical fasteners loaded in the cartridge assembly. Each fastener includes a backspan defining an upper surface and a lower surface; at least a pair of legs depending from the backspan; and at least one contact pad extending from the lower surface to the upper surface of the backspan, wherein at least one of the pair of legs contacts at least one of the contact pads upon a formation thereof during the approximation of the cartridge assembly and the anvil assembly. The electrosurgical system further includes an indicating circuit associated with each of the plurality of fasteners, the indicating circuit including an electrical conduit in electrical contact with a first contact pad of each fastener and an electrical conduit in electrical contact with a second contact pad of each fastener.

In use, upon formation of the fasteners, the legs are formed to at least one of contact a respective contact pad and not contact a respective contact pad, wherein when the respective legs of each fastener properly contact the contact pads a circuit loop of the indicating circuit is established, and when the respective legs of each fastener do not properly contact the contact pads the circuit loop of the indicating circuit is not established.

The circuit loop may be established when the electrical conduit associated with the first contact pad and the electrical conduit associated with the second contact pad are electrically connected to one another when the legs of the fastener properly contact the respective first and second contact pads.

The indicating circuit may include an energy source and an indicator, wherein the indicator activates upon one of a proper formation of the fasteners and not a proper formation of the fasteners. The indicator may activate upon a proper formation of a predetermined number of proper formations of the fasteners.

At least a portion of the backspan of each fastener may be non-conductive. Each contact pad of each fastener may be electrically isolated from the backspan. At least one contact pad of each fastener may extend from the lower surface to the upper surface of the backspan along at least one side surface of the backspan. At least one contact pad of each fastener may extend through the backspan so as to be exposed at the upper surface and the lower surface of the backspan.

Each contact pad of each fastener may be electrically isolated from one another.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 3A is an enlarged schematic illustration of a fastener according to an embodiment of the present disclosure, for use with the surgical instrument of FIG. 1;

FIG. 3A(1) is a bottom plan view of the fastener as shown in FIG. 3A;

FIG. 3A(2) is a cross-sectional view of the fastener as shown in FIG. 3A along the line 3A(2)-3A(2);

DETAILED DESCRIPTION OF EMBODIMENTS

Figure 1:
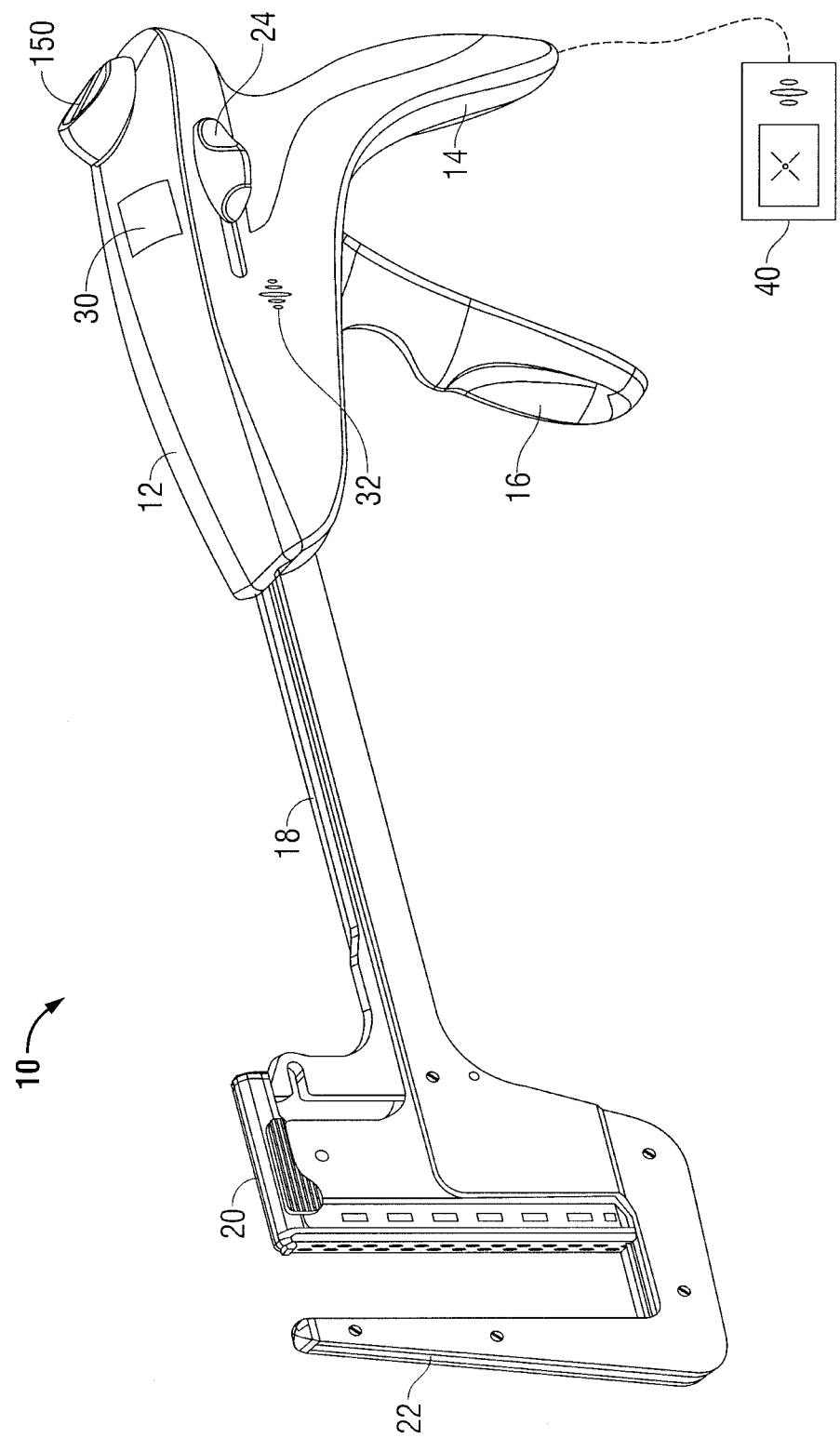
FIG. 1 is a perspective view of a surgical instrument according to an embodiment of the present disclosure.

Preferred embodiments of the presently disclosed surgical instruments and systems will now be described in detail with reference to the drawing figures wherein like reference numerals identify similar or identical elements. As used herein and as is traditional, the term "distal" will refer to that portion which is further from the user while the term "proximal" will refer to that portion which is closer to the user.

A surgical instrument in accordance with an embodiment of the present disclosure is shown generally as 10 in FIG. 1. Surgical instrument 10 includes a body 12 defining a stationary handle 14, a pivotable trigger 16, an elongated central body portion 18, and an end effector including a first member or cartridge assembly 20 and a second member of anvil assembly 22. A thumb button 24 is slidably positioned on each side of body 12. Thumb buttons 24 are movable to manually advance an alignment pin assembly (not shown). A release button 150 is positioned on the proximal end of body 12 and is depressible to allow cartridge assembly 20 to return from an approximated position disposed adjacent to anvil assembly 22 to a position spaced from anvil assembly 22 (as shown).

Figure 2:
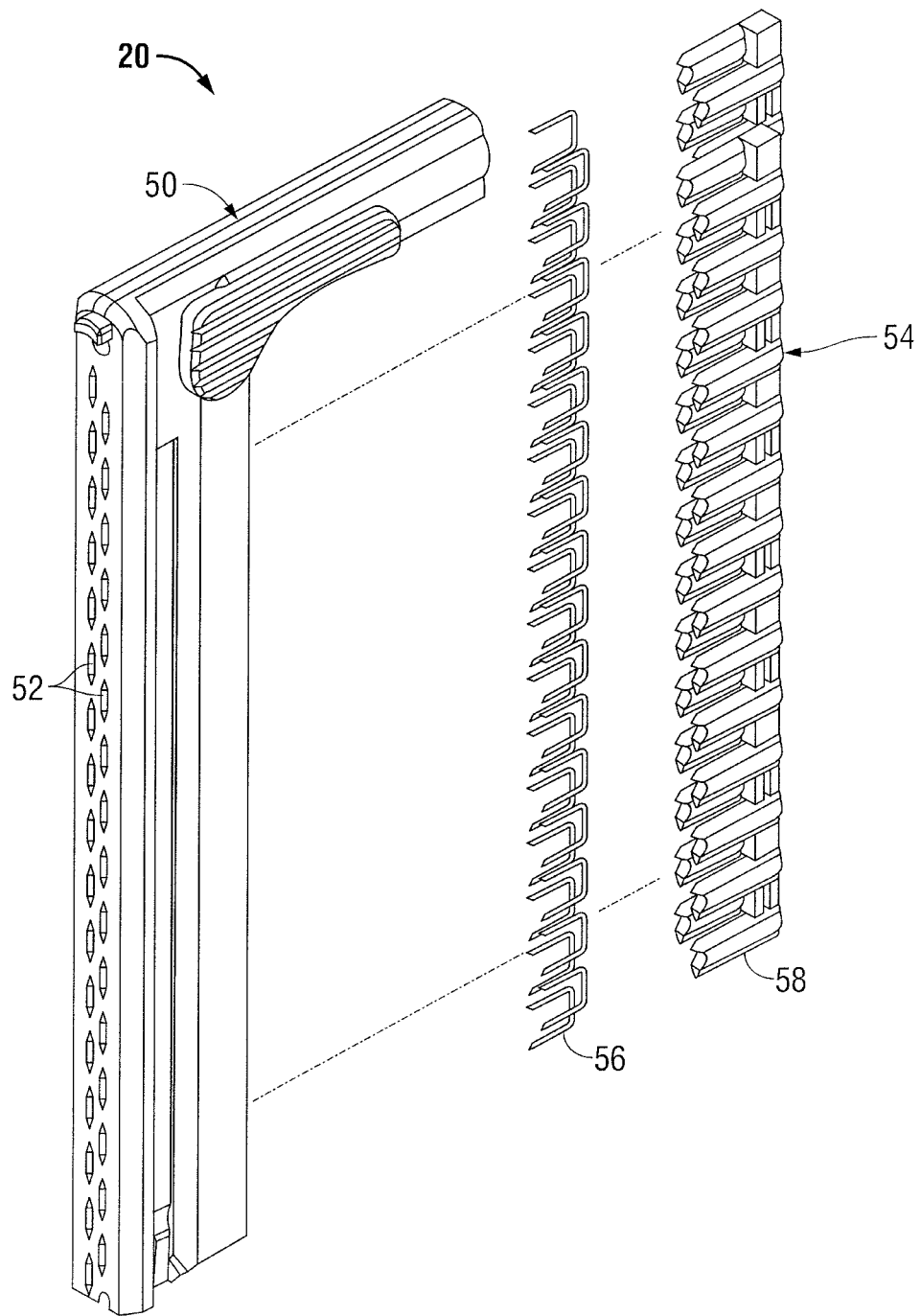
FIG. 2 is an enlarged exploded perspective view, with parts separated, of a staple cartridge assembly for the surgical instrument of FIG. 1.

As seen in FIG. 2, cartridge assembly 20 includes a cartridge 50 having an array of fastener receiving slots 52 formed therein, and a fastener pusher assembly 54 operatively associated with cartridge 50 and including a plurality of pusher members 58. Each pusher member 58 is configured to be slidably received within a respective fastener receiving slot 52. A respective pusher member 58 is positioned behind each fastener 56 in slots 52 such that, in operation, advancement of pusher member 58 effects ejection of fasteners 56 from slots 52. As used herein, fasteners are understood to include and are not limited to, surgical staples, surgical clips, two-part surgical fasteners, surgical tacks, and the like.

Reference may be made to U.S. Pat. No. 6,817,508, the entire content of which is incorporated herein by reference, for a more detailed discussion of the structure and operation of surgical instrument 10.

While a surgical instrument for performing a transverse anastomosis surgical procedure has been shown and described, the present disclosure is not limited to such a surgical instrument. It is contemplated that other surgical instruments may employ the features and concepts of the present disclosure, including and not limited to, open gastro-intestinal surgical instruments, endoscopic gastro-intestinal surgical instruments, and/or end-to-end anastomosis surgical instruments.

As seen in FIG. 3A, a fastener or staple, in accordance with a first embodiment of the present disclosure, is designated as 56. Staple 56 includes a backspan or crown 60 and at least a pair of legs 62 depending from opposed ends of backspan 60. Legs 62 are spaced apart from one another and have an initial, un-formed condition, wherein legs 62 are substantially parallel to one another and substantially orthogonal to backspan 60.

Staple 56 includes at least one, preferably a pair of contact pads 64a, 64b operatively supported on backspan 60. Each contact pad 64a, 64b wraps around a side surface of backspan 60. As best seen in the cross-section view of FIG. 3A(2) as taken along line 3A(2)-3A(2) of FIG. 3A, each contact pad 64a, 64b extends from an upper surface of backspan 60, around a side of backspan 60, to a lower surface of backspan 60 (see FIGS. 3A(1) and 3A(2)). Each contact pad 64a, 64b is fabricated from an electrically conductive, biologically compatible material, such as, for example, stainless steel, titanium or the like. Contact pads 64a, 64b may be electrically isolated or insulated from backspan 60 by a suitable electrically insulative and biologically compatible material or layer 63 which as shown in phantom in FIG. 3A, surrounds the contact pads 64a, 64b.

In one embodiment, backspan 60 may have a substantially flattened profile. It is envisioned that a plane defined by the flattened backspan is substantially orthogonal to a plane defined by the pair of legs 62.

In an embodiment, it is contemplated that backspan 60 is fabricated from a non-conductive or insulative material and legs 62 and contact pads 64a, 64b may be fabricated from an electrically conductive material and biologically compatible material, such as, for example, stainless steel, titanium or the like. Thus, contact pads 64a, 64b are electrically isolated from one another.

Figure 3B:
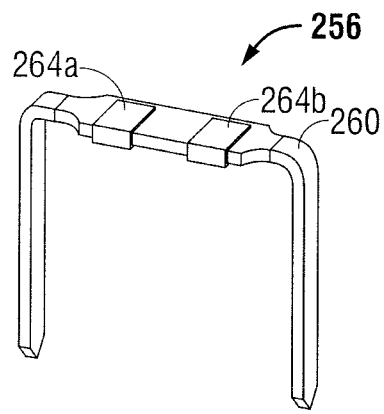
FIG. 3B is an enlarged perspective view of an alternate embodiment of the fastener.

In the embodiment of FIG. 3B, staple 256 is identical to staple 56 except for the configuration of the contact pads 264a, 264b which have a substantially rectangular shape with substantially straight edges wrapping around a side surface of the backspan 260.

Figure 3C:
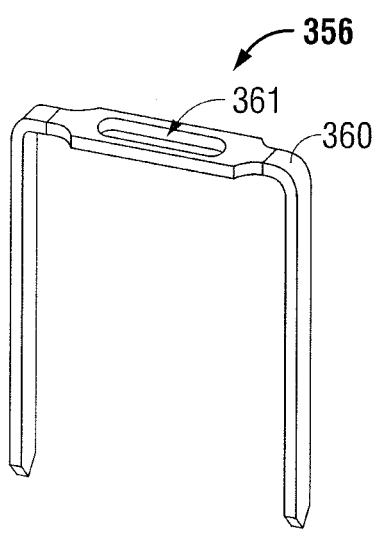
FIG. 3C is an enlarged perspective view of another alternate embodiment of the fastener.
Figure 3D:
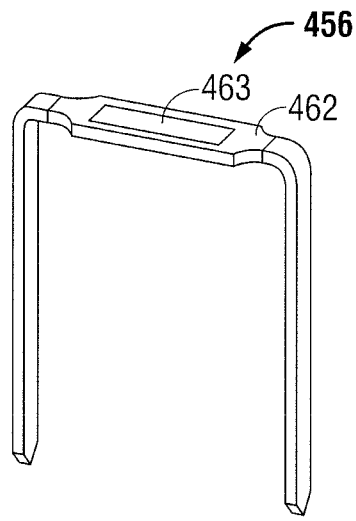
FIG. 3D is an enlarged perspective view of another alternate embodiment of the fastener.

In the embodiment of FIG. 3C, staple 356 has a backspan 360 with a through hole 361. The staple legs, when formed, will extend through the hole 361 to contact conductive pads on the staple pusher. Alternatively, a cap can be provided in the hole as shown in FIG. 3D to fill the hole. Cap 462 is seated within the hole of staple 456. The cap 462 has a contact pad 463 that is pushed up by the formed staple legs to make contact with the pusher contacts.

Figure 4:
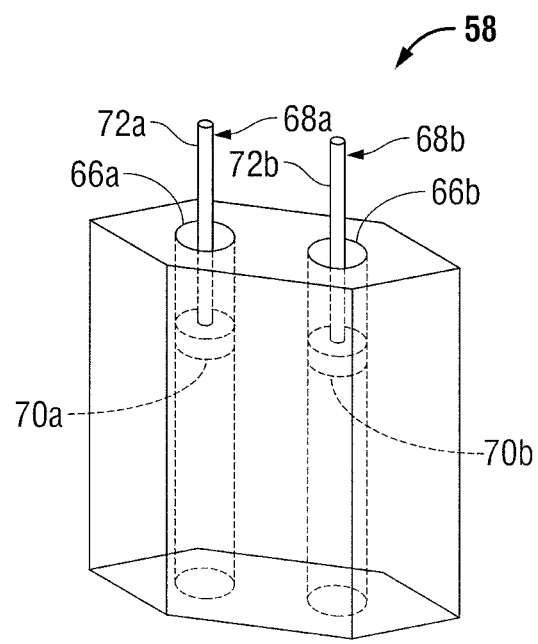
FIG. 4 is a schematic illustration of a pusher according to an embodiment of the present disclosure, for use with the surgical instrument of FIG. 1.

As seen in FIG. 4, each pusher member 58 includes a pair of spaced apart, longitudinally extending lumens 66a, 66b, and a plunger 68a, 68b disposed within each respective lumen 66a, 66b. Each plunger 68a, 68b includes a head portion 70a, 70b, respectively, and a rod portion 72a, 72b extending from each respective head portion 70a, 70b. Head portions 70a, 70b can be in close proximity to a bottom end of respective lumens 66a, 66b.

Plungers 68a, 68b may be fabricated from electrically conductive materials and may be electrically isolated or insulated from one another. For example In operation, as plungers 68a, 68b and rods 72a, 72b remain fixed within lumens 66a, 66b as staple pushers 58 are advanced to fire the staples. In an alternate embodiment, plungers 68a, 68b may be slidably supported in spaced apart lumens 66a, 66b formed in an electrically non-conductive or insulative pusher member 58.

Figure 9:
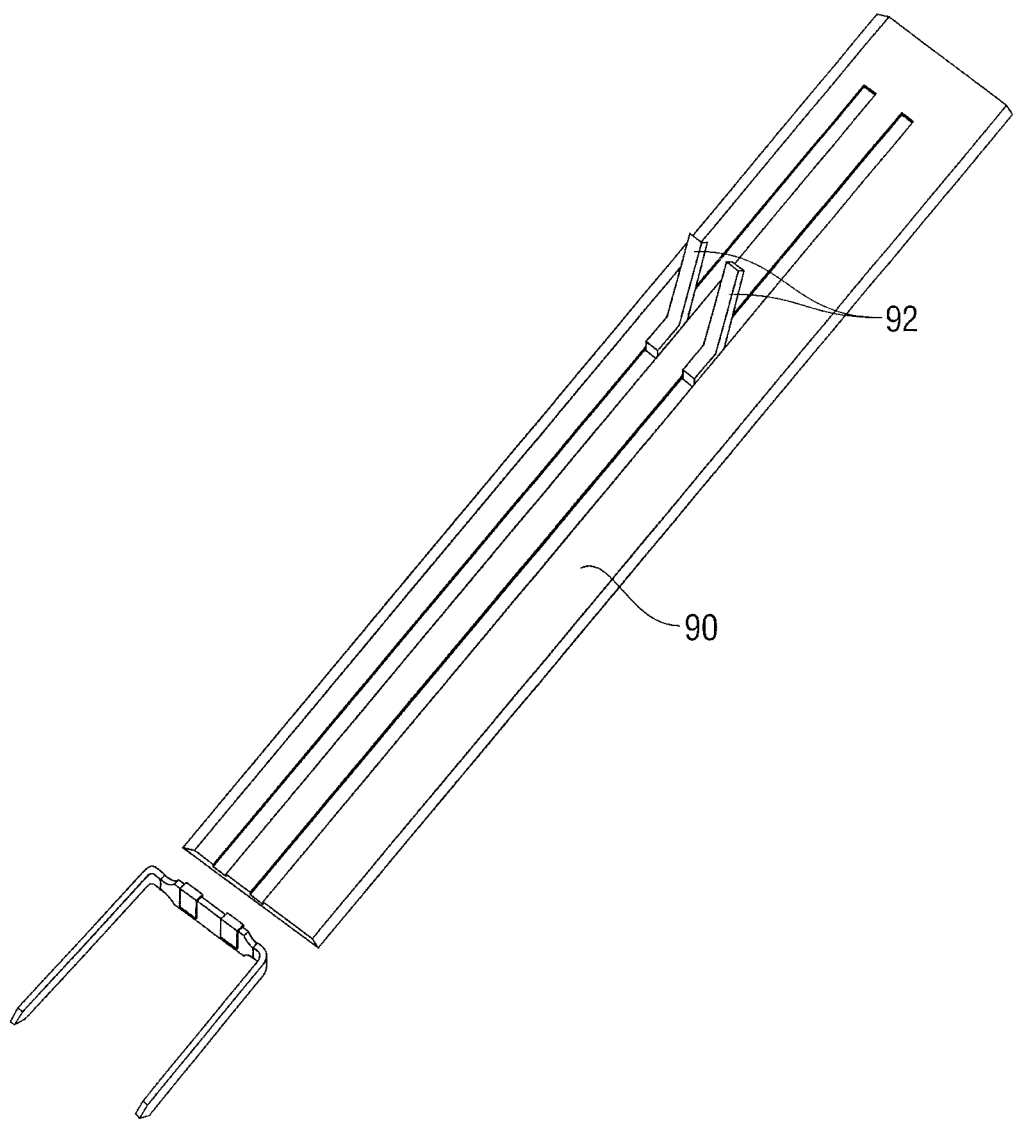
FIG. 9 is a schematic view of an alternate embodiment of a staple pusher.

In the embodiment of FIG. 9, fingers 92 are attached to the cartridge and remain stationary as pusher 90 is advanced to fire the staples.

Figure 5:
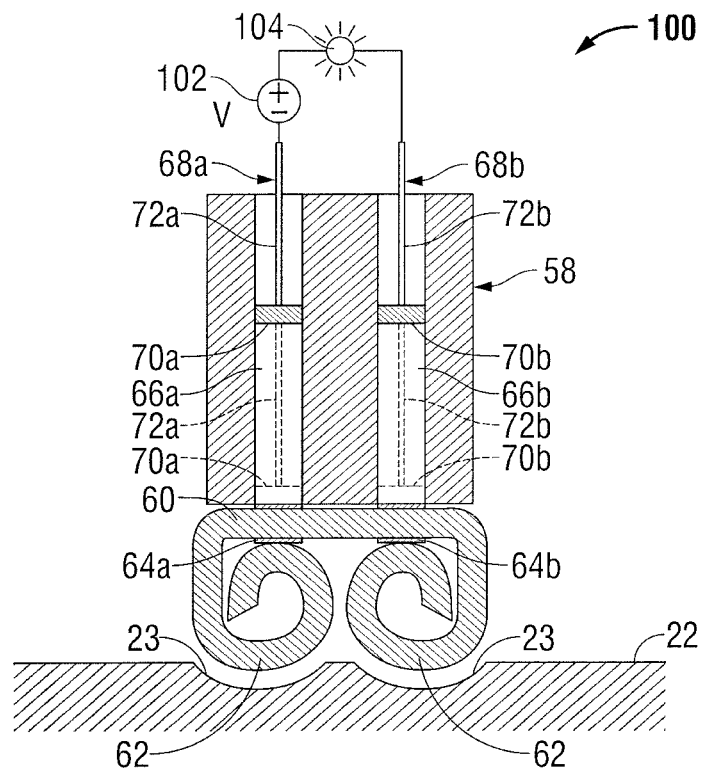
FIG. 5 is a schematic cross-sectional view of the fastener and pusher of FIGS. 3 and 4, operatively associated with one another.
Figure 6:
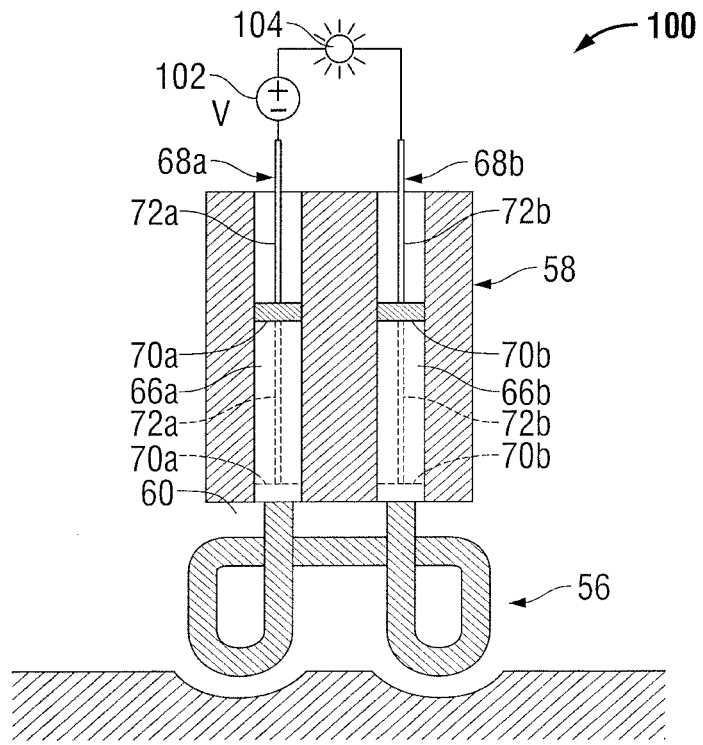
FIG. 6 is a schematic of an electrical circuit according to an embodiment of the present disclosure.

As seen in FIGS. 5 and 6, an indicating circuit 100 is provided which is electrically connected to plungers 68a, 68b. Indicating circuit 100 may include an energy source 102 (e.g., a battery, etc.), and an indicator 104 (e.g., illumination element, light-emitting-diode, etc.) electrically connected to energy source 102. Additionally, a first plunger 68a may be electrically connected to energy source 102 and a second plunger 68b may be electrically connected to indicator 104.

In use, as seen in FIGS. 5 and 6, during a firing of surgical instrument 10, pusher members 58 are actuated to eject, push or otherwise expel staples 56 out of fastener receiving slots 52 (see FIG. 2) and against respective anvil pockets 23 of anvil assembly 22 to form legs 62 of staple 56. As legs 62 of staple 56 are formed, legs 62 are bent towards and against backspan 60. When staple 56 is properly formed legs 62 contact or electrically engage contacts 64a, 64b (or contacts 264a, 264b or pads 210, 220). Note, the legs of staple 356 would contact the conductive pads of the pusher and the legs of staple 456 would contact the cap to move it into engagement with the pusher contact pads to complete the circuit.

When the staple of the foregoing embodiments is properly formed, a circuit loop of indicating circuit 100 is completed and triggers a first particular or unique response signal or indication signal (e.g., an audible signal, a color indication, a graphic or alphanumeric display, or any combination thereof). If a staple 56 is not properly formed, the circuit loop of indicating circuit 100 is not completed and thus a response signal or indication signal is either not triggered or a second particular or unique response signal or indication signal (e.g., an audible signal, a color indication, a graphic or alphanumeric display, or any combination thereof).

The signals generated by indicating circuit 100 may be displayed or broadcast from a visual display 30 and/or a speaker 32 provided on body 12 of surgical instrument 10. Alternatively, the signals generated by indicating circuit 100 may be displayed or broadcast from a separate unit 40, e.g., CPU, monitor, etc., (see FIG. 1) electrically connected to surgical instrument 10.

In operation, each of the foregoing staples (e.g., staple 56) is so monitored in order to determine if staples 56 have been properly formed and/or what percentage of the total number of staples have been properly formed in order to ascertain if an acceptable firing of surgical stapler 10 has occurred. If a percentage of the total number of staples 56 that are properly fired exceeds a predetermined level, then a determination can be made that the stapler firing is acceptable. The predetermined level may depend on the type of surgical procedure, the type of underlying tissue, the biology and medical/physical condition of the patient, the medical history of the patient and/or patient's family, the physical dimensions of the staples, and any other suitable parameters.

In the event that an acceptable firing of surgical instrument 10 has not occurred, the staple line may be reinforced by suturing or by redoing the procedure.

Figure 7:
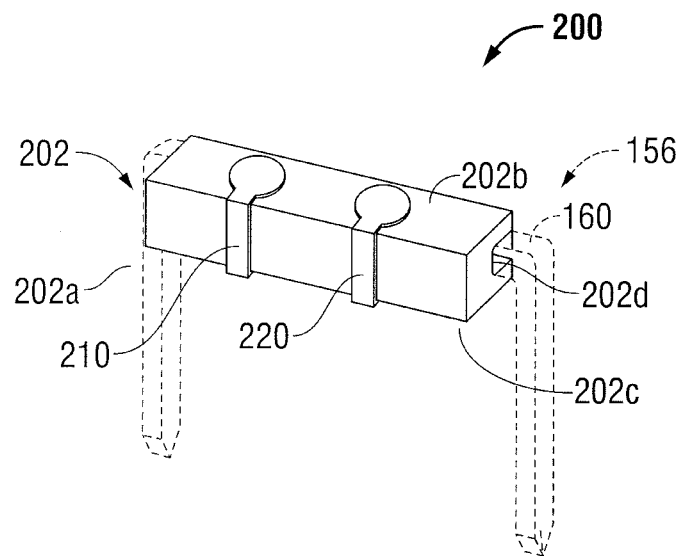
FIG. 7 is a schematic top perspective view of a connector pad assembly, according to an embodiment of the present disclosure, illustrated supported on a surgical staple (shown in phantom)
Figure 8:
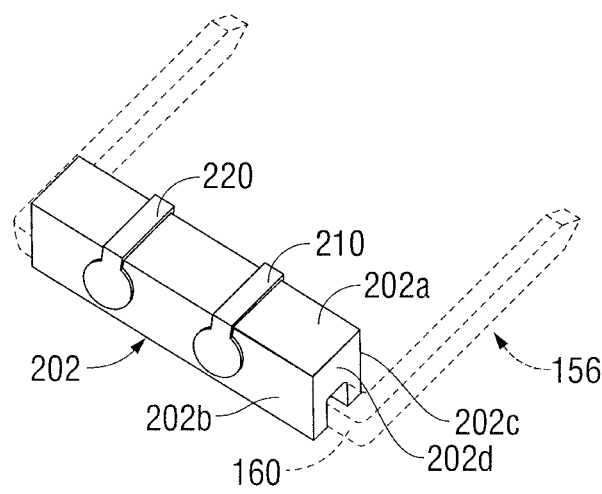
FIG. 8 is a schematic right-side perspective view of the connector pad assembly of FIG. 7.

Turning now to FIGS. 7 and 8, a connector pad assembly, in accordance with another embodiment of the present disclosure, is generally designated as 200. Connector pad assembly 200 may be selectively or fixedly supported on or connector to a backspan 60 of a conventional surgical staple 156. Connector pad assembly 200 may be secured to backspan 160 of surgical staple 156 by a suitable adhesive, by welding, or by an interference, press or friction fit.

Connector pad assembly 200 includes an electrically non-conductive or insulative body portion 202 configured for support or connection to backspan 160 of surgical staple 156. Body portion 202 may be in the form of a U-shaped channel having a back wall 202a, and a pair of spaced apart side walls 202b, 202c extending from back wall 202a and defining a channel 202d therebetween. Channel 202d of body portion 202 is sized and dimensioned to receive backspan 160 of surgical staple 156 therein.

Connector pad assembly 200 further includes a pair of electrical contact pads 210, 220 disposed on or suitably supported on an outer surface of body portion 202. Each contact pad 210, 220 extends from first side wall 202b of body portion 202, across back wall 202a of body portion 202, and to second side wall 202c of body portion 202. Each contact pad 210, 220 is fabricated from an electrically conductive, biologically compatible material, such as, for example, stainless steel, titanium or the like.

In use, a connector pad assembly 200 is attached to a backspan of a conventional surgical staple and the surgical staple, including the connector pad assembly 200 is loaded into staple receiving slots 52 of a cartridge 50 of a surgical stapling instrument 10, including an indicating circuit 200 as described above. The surgical stapling instrument 10 is then use in a surgical procedure, in a manner similar to the method described above. A surgical instrument 10 loaded with surgical staples 56, including connector pad assemblies 200, will function similar to a surgical instrument 10 loaded with surgical staples 56, as described above and thus will not be discussed in greater detail herein.

As various changes could be made in the above constructions without departing from the scope of the disclosure, it is intended that all matter contained in the above description shall be interpreted as illustrative and not in a limiting sense. In the view above it will be seen that several objects of the disclosure are achieved and other advantageous results attained, as defined by the scope of the following claims.

What is claimed is:

1. A surgical fastener, comprising:
   a single backspan defining an upper surface, a lower surface and a pair of side surfaces;
   a pair of legs, each leg of the pair of legs depending from the lower surface of the backspan; and
   at least one contact pad fabricated from an electrically conductive material on the backspan, wherein at least one of the pair of legs is configured to contact the at least one contact pad to provide an indication of formation, wherein the at least one contact pad extends from the lower surface to the upper surface of the backspan along at least one side surface of the backspan; and wherein at least one leg is fabricated from an electrically conductive material and at least a portion of the backspan is non-conductive.

2. The fastener according to claim 1, wherein the non-conductive portion of the backspan electrically isolates the at least one contact pad from a remainder of the backspan.

3. The fastener according to claim 1, wherein the at least one contact pad includes a pair of contact pads, wherein the pair of contact pads is supported on the backspan, wherein each leg contacts a respective contact pad upon proper formation thereof.

4. The fastener according to claim 3, wherein each leg is fabricated from an electrically conductive material.

5. The fastener according to claim 3, wherein one of the pair of contact pads is electrically isolated from the other contact pad.

6. The fastener according to claim 1, wherein the at least one contact pad includes a pair of contact pads, wherein the pair of contact pads is supported on the backspan, wherein only one leg contacts a respective contact pad upon improper formation thereof.

7. The fastener according to claim 1, wherein the at least one contact pad is dimensioned to extend along only one side surface of the backspan.

8. The fastener according to claim 1, wherein the at least one contact pad is free from contact with the legs prior to formation of the staple.

* * * * *